United States Patent [19]

Vaskys et al.

[11] 4,086,666
[45] May 2, 1978

[54] BREAST PROSTHESIS

[75] Inventors: Petras Vaskys, 128 Yew Rd., Cheltenham, Pa. 19012; Arthur M. Pfrommer, Philadelphia, Pa.

[73] Assignee: Petras Vaskys, Cheltenham, Pa.

[21] Appl. No.: 681,803

[22] Filed: Apr. 30, 1976

[51] Int. Cl.² .......................... A61F 1/00; A41C 3/10
[52] U.S. Cl. ........................................ 3/36; 128/462; 128/505; 264/222
[58] Field of Search .............. 3/36; 128/462, 478–481, 128/505

[56] References Cited

U.S. PATENT DOCUMENTS

| | | | |
|---|---|---|---|
| 2,066,503 | 1/1937 | Wiggers | 3/36 |
| 2,580,264 | 12/1951 | Wright et al. | 3/36 X |
| 2,633,440 | 3/1953 | Scholl | 128/505 X |
| 3,811,133 | 5/1974 | Harris | 3/36 |
| 3,911,503 | 10/1975 | Hankin | 3/36 |

FOREIGN PATENT DOCUMENTS 294,665   2/1954   Switzerland .............................. 3/36

Primary Examiner—Ronald L. Frinks
Attorney, Agent, or Firm—Seidel, Gonda & Goldhammer

[57] ABSTRACT

A breast prosthesis in which a negative cast is formed of the wearer's remaining breast and the area of the missing breast. A positive cast is formed of the negative cast and a model is made of the missing breast. A flexible mold is formed over the modeled breast and a portion of the positive cast. The flexible mold is removed and a coating is applied to the positive body cast to form a rear wall with a filling opening. A resilient coating is applied within the flexible mold to form a forward wall of the prosthesis and both the forward and rear walls are secured together. Gel fill is inserted through the filling opening into the interior space formed between the forward and rear walls.

19 Claims, 12 Drawing Figures

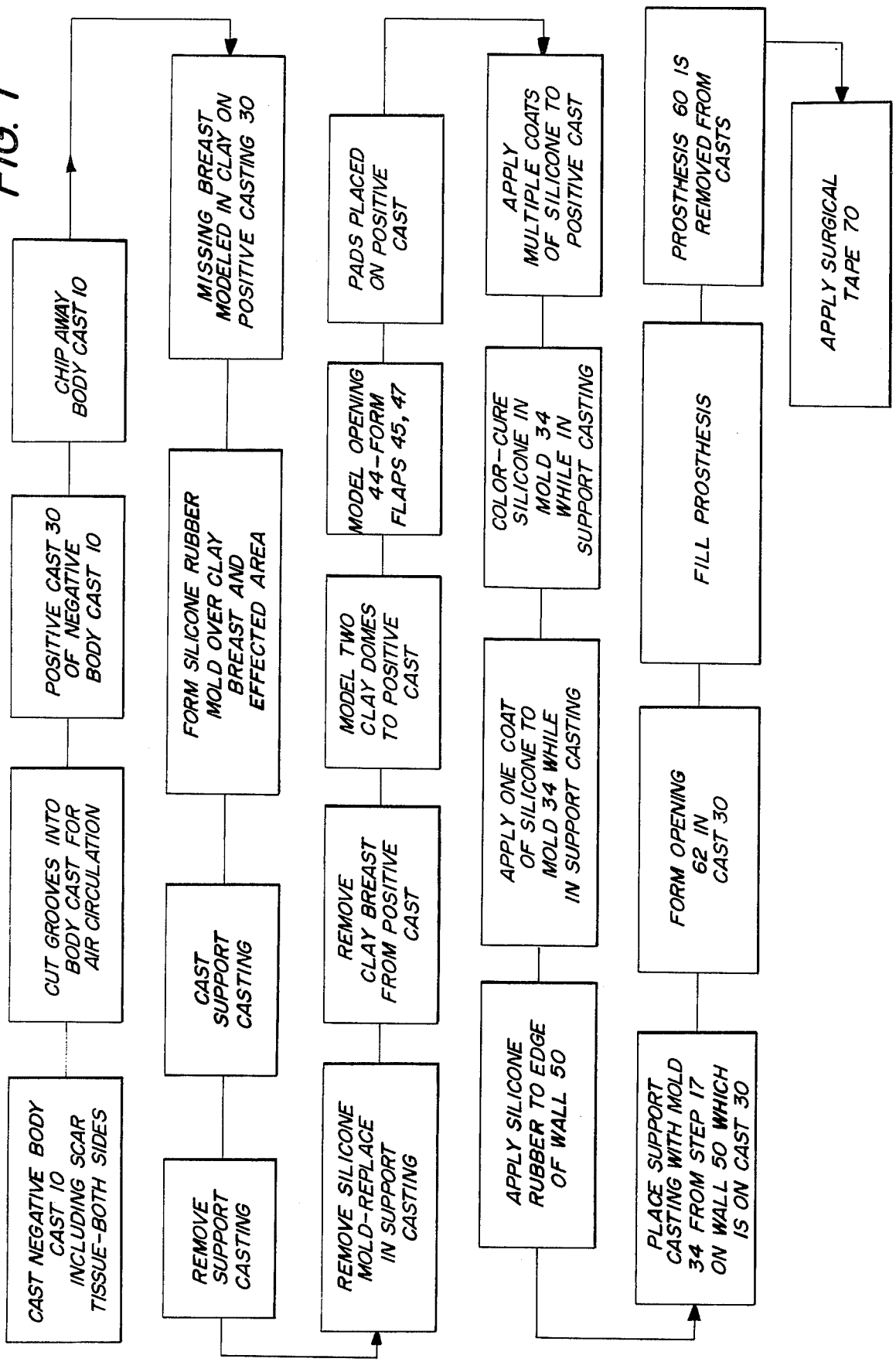

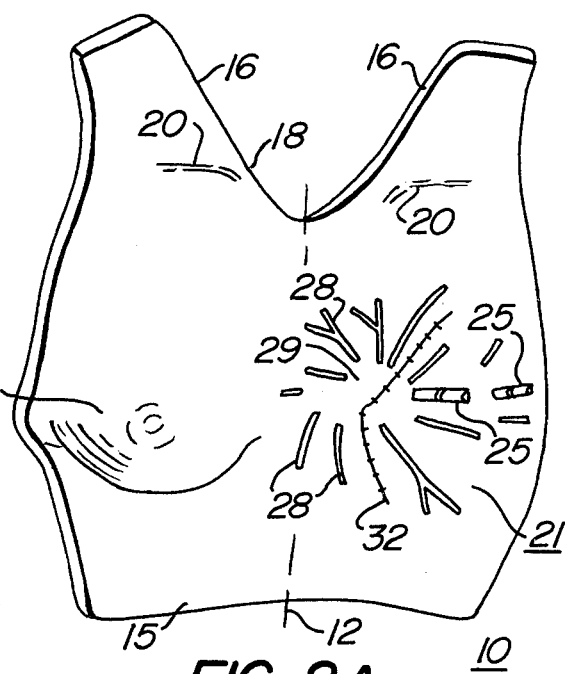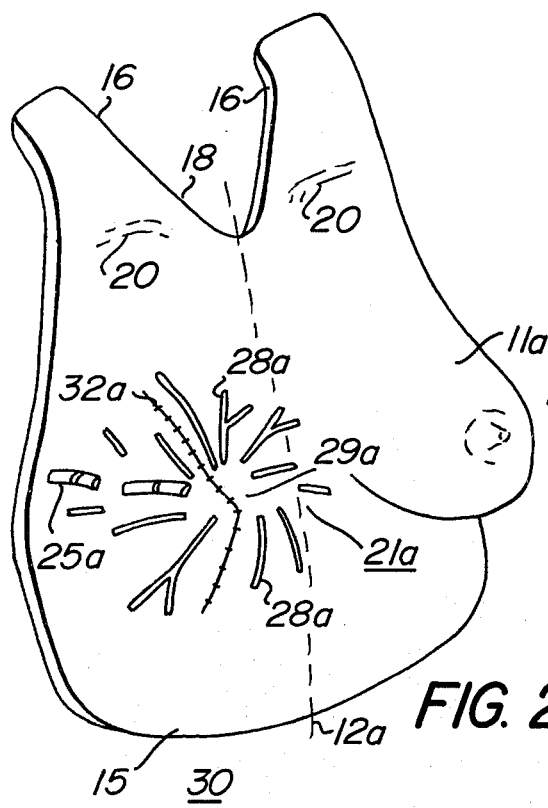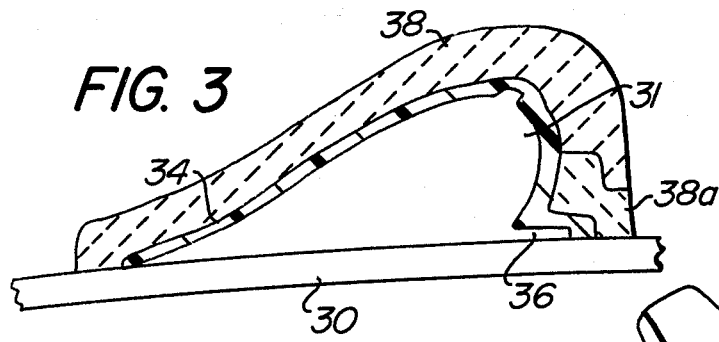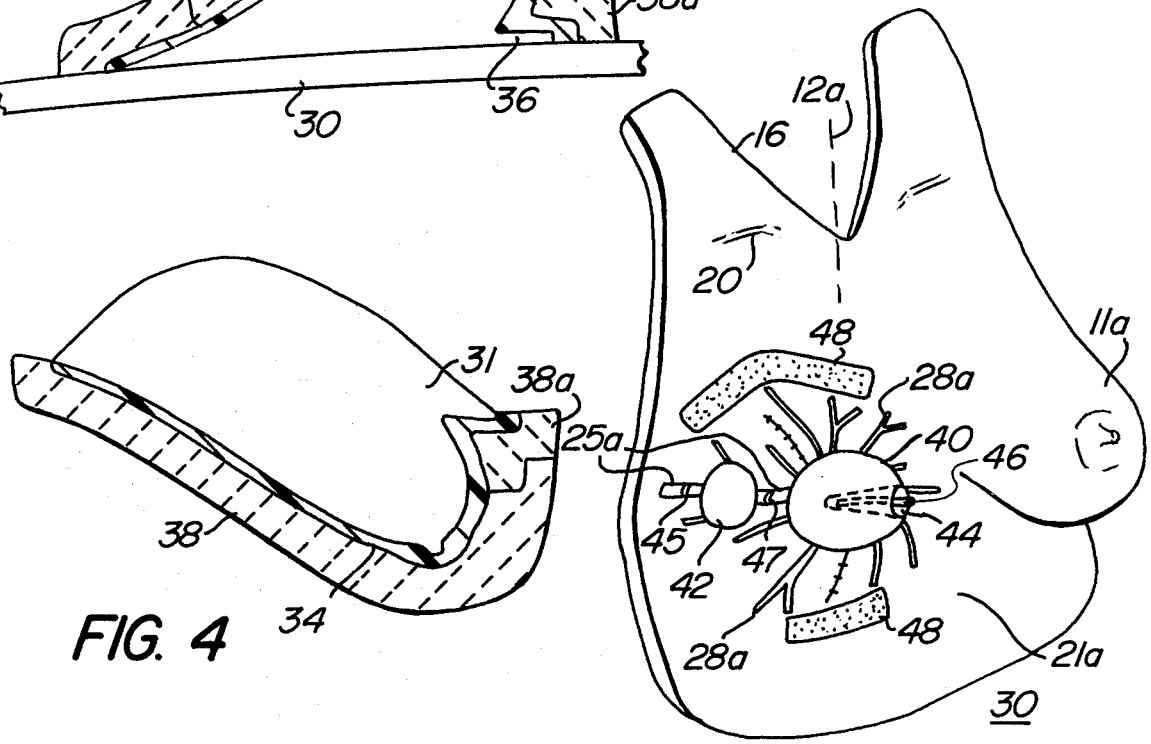

BREAST PROSTHESIS

BACKGROUND OF THE INVENTION

1. Field of the Invention

This invention relates to the field of art of breast prostheses.

2. Prior Art

Prosthetic breasts have been well known for use after mastectomy operations as described for example in U.S. Pat. Nos. 2,482,297; 2,580,264; 2,752,602; 2,814,808; 2,851,692; 2,867,818; 3,196,464; 3,619,819; and 3,811,133.

However, these prior devices have left much to be desired in wearing comfort as well as an exact simulation of the removed breast, the area around the breast and the muscles under the arm in a radical mastectomy. In some instances, the prosthesis device has been filled with a solid or shreaded pellitized foam rubber in an attempt to simulate a breast. However, such foam rubber has not simulated the weight or the movement of a natural breast but merely has simulated softness. While some of these prior devices have used actual weights inside the foam padding, there still has been a lack of simulation of movement with the wearer. Further objections to some prior devices have been that they have slid out of position particularly when the wearer engaged in active sports and even though she were wearing a bra. A still further drawback has been in the coloration and the feel and softness to the touch as to simulate a breast.

Still an additional objection to prior devices has been in discomfort to the wearer. Because air has not circulated behind the prosthesis, perspiration has accumulated causing irritation and general discomfort.

SUMMARY OF THE INVENTION

A method of making a breast prosthesis which comprises the steps of forming a negative cast of the wearer's remaining breast and the area of the missing breast. A positive cast is formed of the negative cast and a model is made of the missing breast. A flexible mold is formed over the modeled breast and a portion of the positive cast. The flexible mold is removed and the modeled breast is discarded. A coating is applied to the positive body cast to form a rear wall of the prosthesis. A resilient coating is applied to the flexible mold to form a forward wall. The forward and rear walls are secured together and gel fill is inserted between the interior space between the forward and rear walls.

BRIEF DESCRIPTION OF THE DRAWINGS

FIG. 1 is a flow chart of the method of making a breast prosthesis according to the invention;

FIGS. 2A-B illustrate perspective views of a negative and a positive body cast according to the method of FIG. 1;

FIGS. 3 and 4 illustrate a cross sectional view and a lower view of the modeled clay breast, mold and support cast;

FIGS. 5 and 6 are perspective views of the positive body cast taken at further steps in the method of FIG. 1;

DETAILED DESCRIPTION

Figure 7:
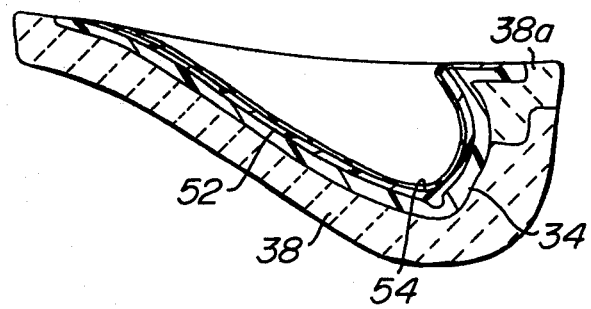
FIG. 7 is a cross sectional view of the support cast, mold, forward wall 52 and layer 54.
Figure 8:
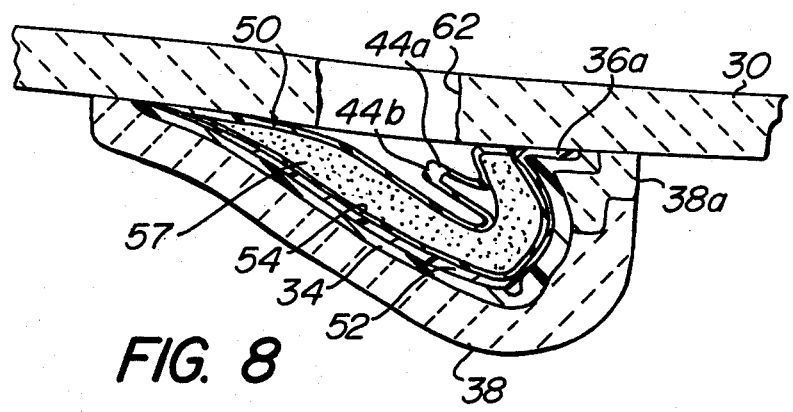
FIG. 8 is a cross sectional view of prosthesis 60 during the filling operation.
Figure 9:
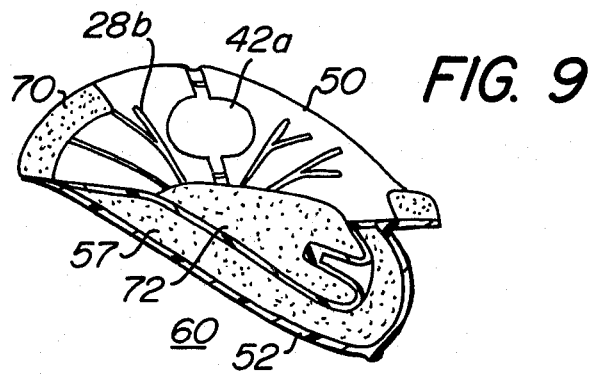
FIG. 9 is a cross sectional view of the filled prosthesis 60 after completion.
Figure 10:
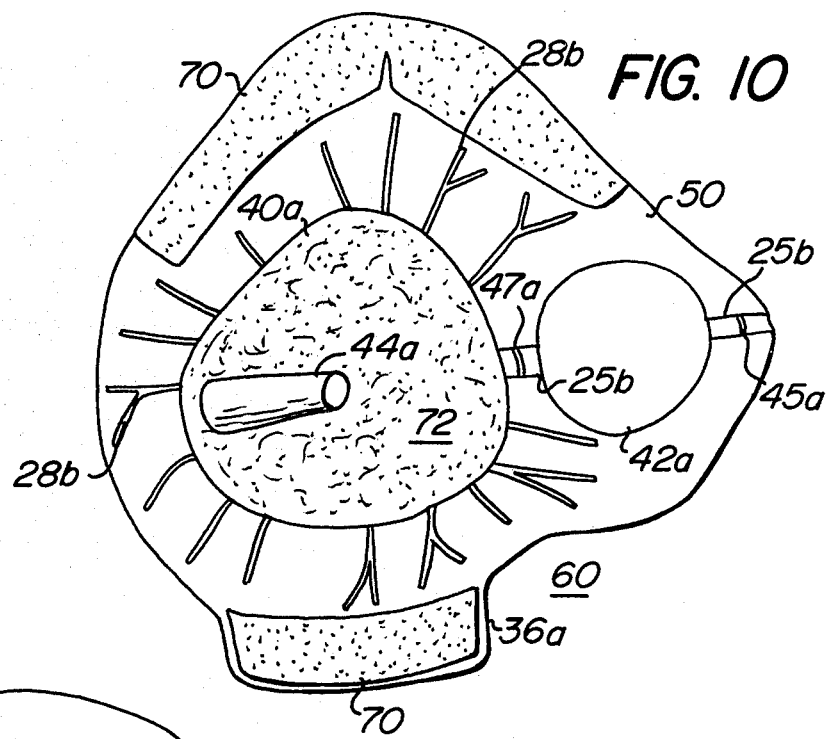
FIG. 10 is an elevation view of the rear wall of the prosthesis.
Figure 11:
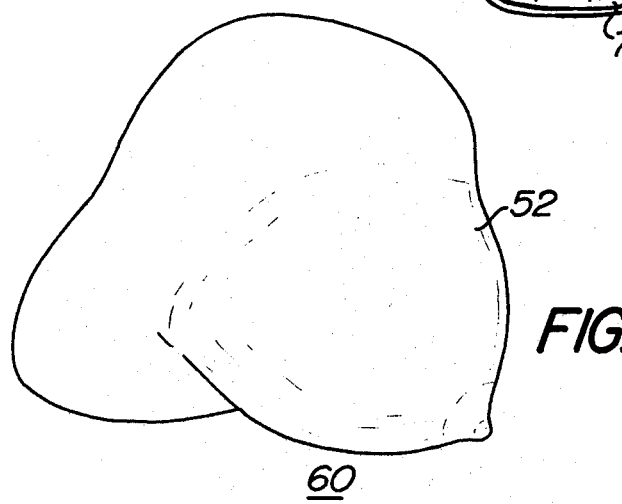
FIG. 11 is a perspective view of the forward wall of the completed prosthesis.

Referring to FIGS. 9-11, there is shown a breast prosthesis 60 which has been made by the method steps 1-21 shown in the flow chart of FIG. 1 and later described in detail with respect to FIGS. 2A-8.

Prosthesis 60 has a rear or body wall 50 which is effective to lock the prosthesis to the body and eliminate slipping and sliding which is particularly a problem when the wearer is very active. Specifically, rear or body wall 50 of prosthesis 60 is contoured as a result of the described molding process exactly to the area from which a breast has been removed. As a result of this exact contour, prosthesis 60 is maintained and locked in position whether the wearer is wearing a bra or not.

Prosthesis 60 has a breathing apparatus formed on the outer surface of rear wall 50 to provide air circulation between the prosthesis and wearer. This avoids irritation and discomfort caused by accumulation of perspiration. Further, rear wall 50 has an integral filling tube 44a which permits the initial insertion of silicone gel fill 57 as well as subsequent addition or deletion of fill.

The outer or forward resilient wall 52 of prosthesis 60 is color matched to the skin color of the wearer and has substantially the same softness since it is made of silicone rubber which has the same texture, softness and resiliency as a real breast. In addition, fill 57 of the prosthesis is silicone gel which provide movement throughout the prosthesis as close as possible to a normal breast. In typical examples, it has been found that depending on the size of the prosthesis, the dead weight thereof may be from one-half to the full weight of the removed breast. Accordingly, the weight of prosthesis 60 may be controlled during the manufacturing operation by increasing or decreasing the size of the breathing apparatus and particularly the size of chambers 40a, 42a.

In this way there is provided a breast prosthesis which comes as close as possible to the removed breast in softness, color, contour and movement. In addition, prosthesis 60 is effectively locked in place due to the contour of wall 50. Additionally, a flap 36a may be provided to be held by a bra when the wearer is wearing a bra.

The following is a series of method steps in the method of making a prosthesis 60.

STEP 1

As shown in FIG. 2A, a waste mold is cast of the woman's body to form a negative body cast 10. The casting is done in pottery plaster of paris mixed with water and reinforced with fiberglass in conventional manner. Body cast 10 extends from the waist 15 to shoulders 16 around neck 18 and includes clavicle 20. Cast 10 includes the entire area around missing breast 21 together with remaining breast 11 (without bra) and under the arm adjacent the missing breast. Lines 32 indicate scar tissue impressions from the mastectomy operation.

The reason that negative body cast 10 includes the clavicle 20 is to identify the actual center line 12 of the breast in the longitudinal dimension of the body. Because of the loss of the breast, it is quite difficult to identify the center of cast 10 without having a reference point provided by the area of clavicle 20.

STEP 2

As shown in FIG. 2A, area 21 of the missing breast (covering substantially all scar tissue 32) is carved by means of conventional plaster of paris implements to form negative casts for forming breathing lines. Specifically, a two section line 25 forms a cast for a main air intake line while lines 28 form casts for air outlet lines. These casts are positioned on negative body cast 10 substantially in the area 21 where a resultant prosthesis 60 would lie against the body of the wearer from whom cast 10 was made. In addition, these casts 25, 28 extend from an imaginary circular section 29, the diameter of which is a function of the size of breast 11. For example, the diameter of section 29 may be 3–5 inches in typical examples.

STEP 3

A positive body cast 30 is made of negative body cast 10. This positive body cast is also accomplished in pottery plaster of paris reinforced with fiberglass. In conventional manner, in the waste mold process, casts 10 and 30 may be separated by sodium silicate or water glass. Thereafter, cast 10 is chipped off (STEP 4) and the remaining cast is a positive body cast 30 as shown in FIG. 2B having a positive impression 11a of breast 11 and positive impressions 25a, 28a of the breathing lines.

STEP 5

The missing breast is then modeled in clay in a manner so that it matches breast 11a. The modeling is done by a sculptor on top of area 21a and positive impressions 25a, 28a of the breathing lines. This modeling is done by eye and the sculptor attempts to match breast 11a so that modeled breast 31, FIG. 3, is an almost exact copy of the missing breast based upon the sculptor's impression of positive cast breast 11a. Since cast 10 has been made without a bra, then it will be understood that modeled breast 31 is being modeled to hang naturally without a bra.

In addition, breast 31 is modeled to have a flap 36 approximately 1/32 inch thick, 2 inches wide in the transverse dimension of the body and ½ inch long extending from the bottom of breast 31 in the longitudinal dimension of the body.

STEP 6

A silicone rubber model 34 is then formed over modeled breast 31 on cast 30 to cover all of effective area 21a. Further mold 34 may extend in particular examples, all the way up to the shoulder in order to blend the resultant prosthesis 60 onto the body of the wearer. The silicon rubber may be Dow Corning "SILASTIC G" type silicon rubber which is relatively slow setting. The thickness of mold 34 may be about ⅛ inch thick.

STEP 7

A support casting 38, 38a is made in conventional manner of plaster of paris to cover rubber mold 34 and may be approximately ½ to ¾ inch thick. Support casting 38, 38a may be either one piece or cut to form two sections, as illustrated. Second section 38a of the support casting is molded to assist in molding a sagging breast. Thus, first section 38 is undercut and section 38a is allowed to be removed separately and possibly avoid breaking of the casting.

STEP 8

Support casting 38, 38a alone is removed and turned concave side up.

STEP 9

Silicon rubber mold 34 alone is removed and replaced back in support casting 38, 38a as illustrated in FIG. 4.

STEP 10

Modeled clay breast 31 is removed from positive body cast 30 and discarded.

STEP 11

Area 21a on cast 30 is first cleaned. Two domes to form a part of the breathing apparatus are modeled in clay on cavity surface 21a as illustrated in FIG. 5. Specifically, a main dome 40 is modeled in clay over circular area 29a and provides a major portion of the breathing apparatus. It will be understood that the size of dome 40 is a function of the size of the breast. Dome 40 is generally modeled to resemble generally a smaller version of modeled breast 31.

It has been found preferable to have the distance between forward wall 52 of breast prosthesis 60 (FIG. 9) and dome 40 be at least ½ inch. It is in this way that a substantially large breathing apparatus is provided.

In addition, a small dome 42 is modeled in clay at an intermediate point in line 25a. Dome 42 may be about 1½ inch in diameter and about a ¼ inch high in the center. Dome 42 may be positioned substantially under and slightly forward of the arm of the wearer.

STEP 12

A funnel shaped opening 44 is modeled in dome 40. The mouth of opening 44 is formed at the surface of dome 40 with the open mouth substantially facing center line 12a. A short metal rod 46 is inserted in the funnel shaped opening 44.

In order to provide flaps, diagonal cuts 45, 47 are formed in positive impressions 25a. Each of cuts 45, 47 are at an angle of about 35° between a plane formed by cast 30 and a plane facing away from breast 11a. In this manner, there are formed flapper valves in the resultant breathing apparatus. Accordingly, with normal body movement, pumping action is provided and air tends to travel from the exterior of prosthesis 60 through main air intake line 25b (FIG. 10) into small cavity 42a and from small cavity 42a into large cavity 40a and thence out through lines 28b.

STEP 13

Two or more pads 48 according to the size of the breast prosthesis 60 are placed on cast 30 at substantially the outer portions of area 21a. Pads 48 may be made of sheet vinyl or plastic and are just laid on positive cast 30.

STEP 14

Figure 6:
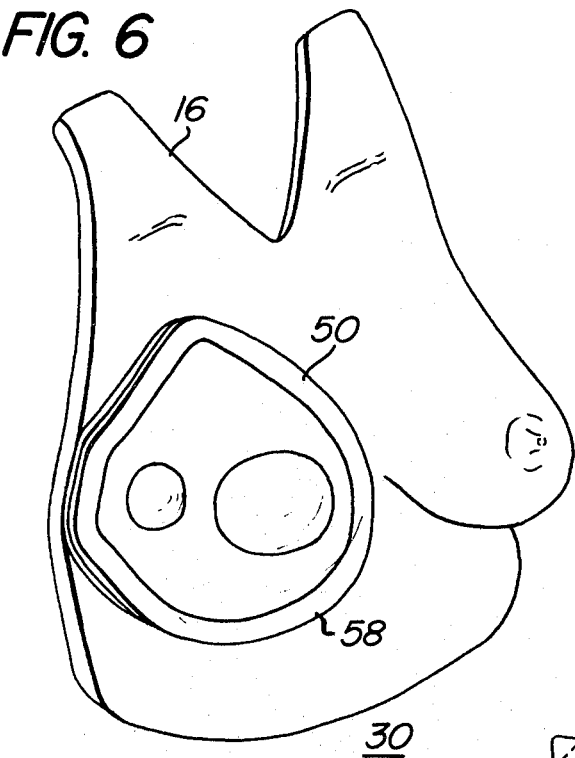

Prosthesis 60 is now ready to be cast over the area 21a shown in FIG. 5. Preferably, three coats of silicone rubber of the type previously described are applied over area 21a and domes 40, 42 to form a rear or body wall 50 as shown in FIG. 6. It will be understood that these coatings of silicone rubber are colored to resemble skin tone of the wearer by conventional means and then cured.

At least two coats may be preferably used for rear wall 50 in order to achieve the necessary thickness to hold the form of prosthesis 60 and maintain proper impression of the body. In this way rear wall 50 is sufficiently thick to maintain the form of the woman's cavity formed by the missing breast while outer or forward wall 52 is soft and lifelike and able to fit the form of the bra. Thus, inner wall 50 supports the rear section of prosthesis 60 and provides structural integrity.

STEP 15

With mold 34 within support casting 38, 38a as shown in FIG. 4, a mold release agent is sprayed into the mold. Thereafter, colored silicone rubber is painted onto mold 34 in the area of the nipple and aurora to simulate the coloring of the wearer. In addition, silicone rubber tinted to the color of veins are painted onto mold 34. This painting material is first semicured.

STEP 16

A coat or layer of silicone rubber of the type previously described of skin color is then applied to the entire inside of mold 34. It is in this way that outer or forward wall 52 of prosthesis 60 is formed with the proper coloration and permanently molded as shown in FIG. 7.

The silicone rubber may have a tendency when punctured to form a running tear. Accordingly, it may be desirable to add a further layer of material 54 on an inner surface (remote from mold 34) of the layer of silicone rubber 52 while in the semicured state. Material 54 may be woven Dacron (Mohawk D118) which is bondable to the silicone rubber. In this way layer 54 and wall 52 would be thin and have good tear strength while still maintaining the necessary soft feel.

STEP 17

A narrow border layer 58 of silicone rubber is applied to the inner surface of wall 50 as shown in FIG. 6. Layer 58 is adjacent the outer edge of wall 50.

STEP 18

While the inner surface of forward wall layer 52 and edge 58 are still sticky, support casting 38, 38a carrying rubber mold 34, wall 52 and layer 54 (FIG. 7) are placed onto wall 50 with wall 50 maintained on cast 30. In this step, cast 30 may be placed with wall 50 facing upwardly and cast 38, 38a is placed on top of cast 30. With the walls placed together, border 58 and the adjacent edge of wall 52 are sealed in conventional manner.

STEP 19

An opening 62 is formed through cast 30 from the rear thereof as illustrated in FIG. 8. In this way there is access to filling tube or opening 44a which was formed by funnel shaped opening 44 in dome 40. FIG. 5 shows rod 46 in place and prosthesis 60 unfilled while FIG. 8 shows the prosthesis filled.

STEP 20

Rod 46 is removed and prosthesis 60 is now ready for filling. Casts 30 and 38, 38a are positioned so that cast 38 is positioned downwardly from cast 30. Silicone gel is fed as fill 57 through opening 62, filling tube 44a and into the interior space or chamber formed by walls 50, 52. The silicone gel may be 619 GE or other gels such as surgical gels made by Dow Corning.

Since prosthesis 60 is being filled while it is held between casts 30 and 38, 38a, there is assurance that the shape of the prosthesis will not change. In this way, both forward wall 52 and rear wall 50 are maintained in shape by the respective casts. After filling, tube 44a is sealed with silicone rubber to form a stopper or plug 44b.

It will be understood that fill 57 may be added or removed as desired by use of a hypodermic needle inserted through plug 44b. This is particularly important if the wearer loses or gains weight. Such adding or removing is preferably performed by the maker of the unit.

STEP 21

Prosthesis 60 is now ready to be removed from casts 30 and 38, 38a.

STEP 22

Two sided adhesive surgical tape 70 is applied as required over pads 48 positioned adjacent outer edges of wall 58. Pads 48 permit such conventional two sided tape to adhere to the prosthesis since this tape would not normally adhere to a silicone rubber surface 50. The purpose of tape 70 is to adhere to the wearer so that the edges of prosthesis 60 are more exactly contoured to the body.

In normal usage, it will be understood, the wearer may not desire to use tape 70 particularly if the wearer is using a bra. Accordingly, tape 70 may easily be removed. However, when not wearing a bra, the wearer would normally use tape 70 so that the contour is more faithfully adhered to. Further, when wearing a bra, flap 36a is held in position by the bra for added support of prosthesis 60.

In addition, makeup may be applied to the outer edge of wall 52 in order to blend in the color of wall 52 with the body tone.

A sponge material 72 may be formed to conform with cavity 40a and then placed therein in order to absorb perspiration and to prevent the possibility of prosthesis 60 collapsing into cavity 40a. It will be understood that sponge 72 may be formed by cutting sponge material or by casting sponge material within the cavity 40a itself.

In another embodiment of the invention, woven Dacron of the type previously described, may be applied to at least one layer of silicone rubber to form wall 50. Specifically, pieces of woven Dacron would be arranged around and not covering domes 40, 42 to form an additional layer. In this manner, the resultant wall 50 may be formed of less thickness of rubber for less weight, but with added strength.

The operation of the breathing apparatus will now be explained. The normal body movements of the wearer tends to circulate air. For example, when the wearer moves her arm, she may effectively actuate chamber or cavity 42a as a pump to pull air in through air intake line 25b into cavity 42a and then through the other air intake line 25b into chamber or cavity 40a. Flapper valves 45a, 47a to a degree may prevent the air from flowing in the reverse direction. Once in cavity 40a, air is then pumped out through lines 28b. It is in this way that small chamber 42a may act as a pump circulating air from the outside and through the cavities and out lines 28b. Further, it is in this way that sponge 72 is provided with fresh air.

The air circulation may also be provided when the wearer wears a bra. When she inhales, the wearer's chest expands tending to compress prosthesis 60 between chest and bra forcing or pumping air out of chambers 40a, 42a through the lines. When the wearer exhales, prosthesis 60 returns to its original shape thereby filling chambers 40a, 42a with outside air. The same action may occur when the wearer bends.

As previously described, negative body cast 10 is made of an unsupported breast and clay breast 31 is made to correspond with positive cast (unsupported) breast 11a. However, it will be understood that a modeled clay breast may be modeled in clay to represent a bra supported breast according to the eye of the scupltor. Thus, it will be understood that with modeled breast 31 representing a bra supported breast prosthesis 60 will then take the form of a lifted breast corresponding to wearing a bra. All of the other steps in the method would be similar.

In order to assist the scupltor in visualizing a breast that is bra supported, an additional negative cast may be made of the wearer in which the remaining breast 11 is supported by a bra. A positive impression is then made of such negative cast and thus the sculptor may more easily model a bra supported clay breast 31. This is particularly important in the case of a wearer who has a sagging breast. Alternatively, measurements may be made of the bra supported breast and then these measurements would be helpful to the sculptor in modeling a clay breast to represent a bra supported breast.

In a bilateral mastectomy, the foregoing method steps may also be followed to produce a bilateral prosthesis with the following changes. Since both breasts have been removed, both sides of cast 30 have respective lines 25a, 28a, domes 40, 42, etc. Further, it would be necessary to model two clay breasts 31 on positive body cast 30. It will be understood that the breasts may be modeled as desired by the wearer and the sculptor.

What is claimed is:

1. A breast prosthesis comprising a cavity formed between a forward wall shaped in the form of a breast and a rear wall shaped to conform with the area of a missing breast, at least the forward wall being made of soft resilient material having a color which substantially simulates the color of skin, gel fill within the cavity, said rear wall having at least one chamber formed therein, said chamber being open at one end and formed within the rear wall with the chamber opening adjacent the wearer when the prosthesis is worn to provide for air circulation between the prosthesis and the wearer, breathing lines formed in the rear wall extending from the chamber along the rear wall toward the outer edge of the prosthesis whereby air is circulated between the chamber and through the lines, an additional chamber open at one end and formed in the rear wall with the opening adjacent the wearer, and an inlet line formed in the rear wall and extending from an edge of the prosthesis into the chamber and from the additional chamber to the chamber.

2. The breast prosthesis of claim 1 in which there is provided sponge material disposed within said chamber for absorbing perspiration of said wearer.

3. The breast prosthesis of claim 2 in which there is provided a filling tube formed in said chamber and extending through said rear wall for inserting and removing gel from said prosthesis.

4. The breast prosthesis of claim 3 in which a flap is formed on a lower edge of said prosthesis which is engaged by the bra of the wearer for added support of the prosthesis.

5. The breast prosthesis of claim 4 in which strips of material are fixed to said rear wall adjacent outer edges thereof and adapted to adhesively receive two sided adhesive tape for better securing the prosthesis to the body of the wearer.

6. A breast prosthesis comprising a forward wall shaped like a breast, a rear wall connected along its periphery to the forward wall defining a cavity between the forward and rear walls, means simulating breast tissue filling the cavity, the front and rear walls being made of soft resilient material which simulates human skin, a generally hemispherical preformed concave chamber formed in a portion of the rear wall, perspiration absorbing means disposed within the chamber, and air communication means in the rear wall extending between the chamber and an outer edge of the rear wall.

7. A breast prosthesis according to claim 6 further comprising valve means formed in the rear wall for introducing the means simulating breast tissue into the cavity.

8. A breast prosthesis according to claim 7 wherein the valve means is self-sealing.

9. A breast prosthesis according to claim 7 wherein the soft resilient material which simulates human skin is a silicone rubber and the means simulating breast tissue is a silicone gel.

10. A breast prosthesis according to claim 6 wherein the perspiration absorbing means is a sponge material having a shape generally conforming to the chamber.

11. A breast prosthesis according to claim 6 wherein the air communication means is preformed in a portion of the rear wall.

12. A breast prosthesis according to claim 11 wherein the air communication means comprises two channels preformed in the rear wall radially extending between the chamber and outer edges of the rear wall.

13. A breast prosthesis comprising a forward wall shaped like a breast, a rear wall connected along its periphery to the forward wall, the forward and rear walls defining a cavity therebetween, means for simulating breast tissue filling the cavity, the front and rear walls being made of a soft resilient material which simulates human skin, a preformed concave chamber formed in a portion of the rear wall, perspiration absorbing means disposed within the chamber, and air communication means in the rear wall extending between the chamber and an outer edge of the rear wall, the air communication means being preformed in a peripheral portion of the rear wall.

14. A breast prosthesis according to claim 13 further comprising valve means formed in the rear wall for introducing the means simulating breast tissue into the cavity.

15. A breast prosthesis according to claim 14 wherein the valve means is self-sealing.

16. A breast prosthesis according to claim 13 wherein the soft resilient material which simulates human skin is a silicone rubber and the means simulating breast tissue is a silicone gel.

17. A breast prosthesis according to claim 13 wherein the perspiration absorbing menas is a sponge material having a shape generally conforming to the chamber.

18. A breast prosthesis according to claim 13 wherein the air communication means comprises two channels preformed in the rear wall radially extending between the chamber and outer edges of the rear wall.

19. A breast prosthesis according to claim 13 wherein flap means for additionally supporting the prosthesis in a brassiere is formed on the prosthesis.

* * * * *